(12) United States Patent
David et al.

(10) Patent No.: US 6,716,215 B1
(45) Date of Patent: Apr. 6, 2004

(54) CRANIAL DRILL WITH STERILE BARRIER

(75) Inventors: John David, Melbourne, FL (US); Matthew S. Solar, Melbourne, FL (US); Gerald W Mills, Palm Bay, FL (US)

(73) Assignee: Image-Guided Neurologics, Melbourne, FL (US)

( * ) Notice: Subject to any disclaimer, the term of this patent is extended or adjusted under 35 U.S.C. 154(b) by 381 days.

(21) Appl. No.: 09/699,044

(22) Filed: Oct. 27, 2000

Related U.S. Application Data

(60) Provisional application No. 60/162,492, filed on Oct. 29, 1999.

(51) Int. Cl.$^7$ .............................................. A61B 15/02
(52) U.S. Cl. ...................... 606/80; 433/116; 600/130
(58) Field of Search .................. 606/80, 130; 433/116

(56) References Cited

U.S. PATENT DOCUMENTS

| | | | | |
|---|---|---|---|---|
| 1,539,253 A | * | 5/1925 | Fuller .......................... | 156/218 |
| 3,955,284 A | | 5/1976 | Balson .......................... | 32/27 |
| 4,456,010 A | | 6/1984 | Reimels et al. ............ | 128/310 |
| 4,795,343 A | | 1/1989 | Choisser ..................... | 433/116 |
| 4,830,001 A | | 5/1989 | Walus ......................... | 128/310 |
| 5,269,733 A | | 12/1993 | Anthony, III ............... | 475/331 |
| 5,380,333 A | | 1/1995 | Meloul et al. ................ | 606/80 |
| 5,590,655 A | * | 1/1997 | Hussman ..................... | 600/414 |
| 5,728,106 A | * | 3/1998 | Misko et al. ................ | 606/130 |
| 5,865,571 A | | 2/1999 | Tankala et al. | |
| 5,868,750 A | * | 2/1999 | Schultz ....................... | 606/104 |

\* cited by examiner

*Primary Examiner*—John Mulcahy
(74) *Attorney, Agent, or Firm*—Schwegman, Lundberg, Woessner & Kluth, P.A.

(57) ABSTRACT

A medical device is provided comprising a MRI compatible cranial drill having a removable sterilizable drill bit and a sterile barrier. The sterile barrier has an interior portion, a proximal end, a distal end, a proximal opening at the proximal end and an opening at the distal end. The opening at the distal end further comprises an aperture. The drill is insertable into the proximal opening, the aperture being constructed and arranged to seal around the drill bit such that the drill is enclosed in the interior portion of the sterile barrier and only a portion of the sterile drill bit extends exteriorly of the barrier. In one embodiment, the medical device includes a MRI compatible adjustable depth stop which limits and defines depth of penetration of the drill. In one embodiment the present invention provides a method for providing access to a body of a surgical patient, which includes providing a medical device comprising in combination a MRI compatible drill and a sterile drill bit, providing a locking trajectory guide, mounting the trajectory guide on the patient's body, selecting a predetermined depth and adjusting the depth stop to the predetermined depth, advancing the medical device to the body and aligning it with the trajectory guide, utilizing the medical device to cause the sterile drill bit to penetrate the body the predetermined depth to which the depth stop is adjusted, and removing the sterile drill bit from the body. In one embodiment, the medical device includes a sterile barrier.

25 Claims, 20 Drawing Sheets

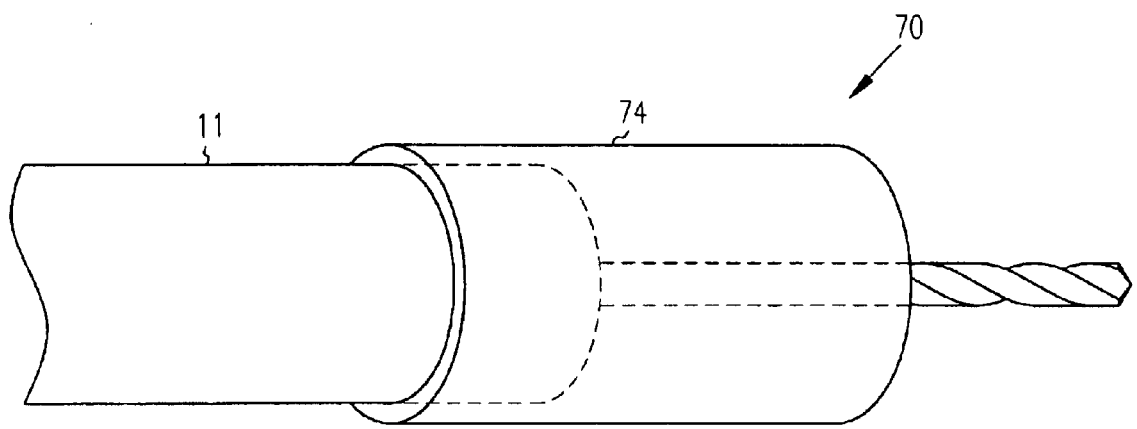
FIG. 14A
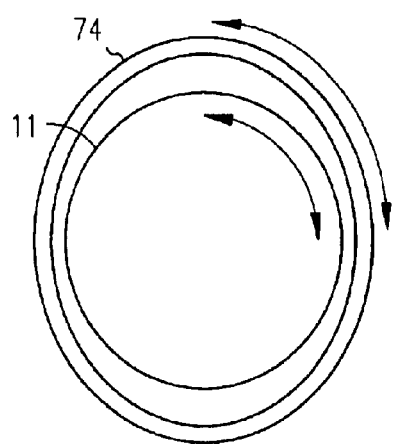 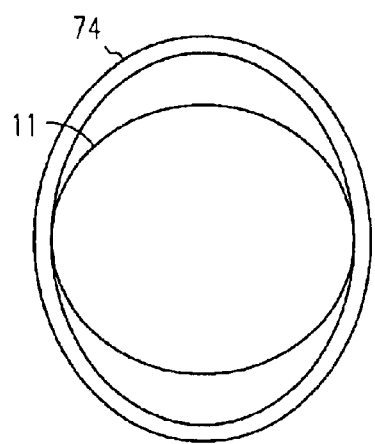
FIG. 14B  FIG. 14C

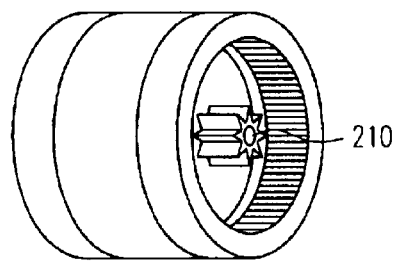
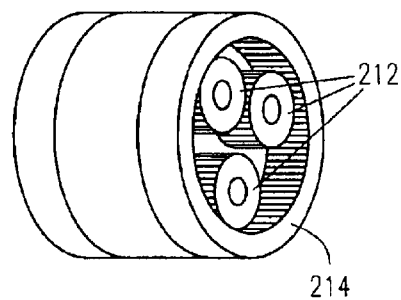
FIG. 19A  FIG. 19B
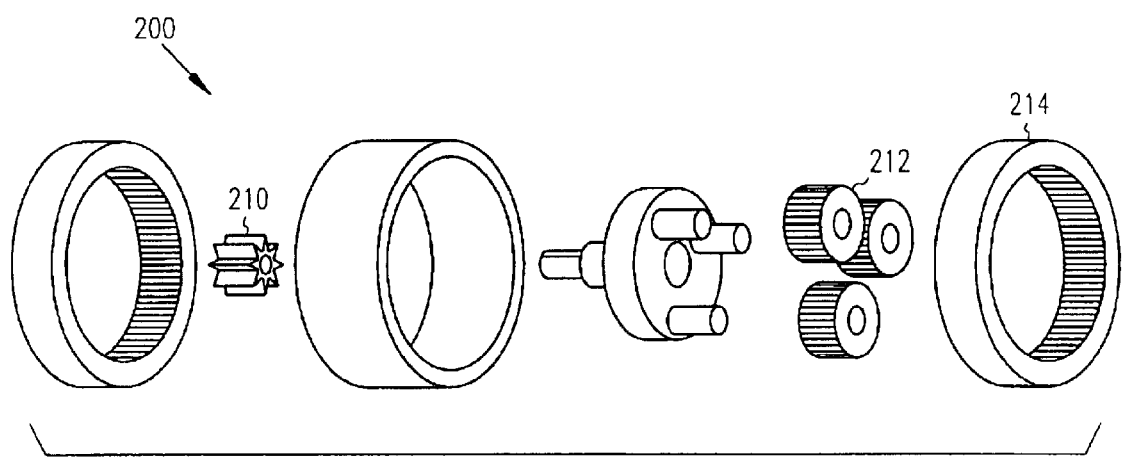
FIG. 19C

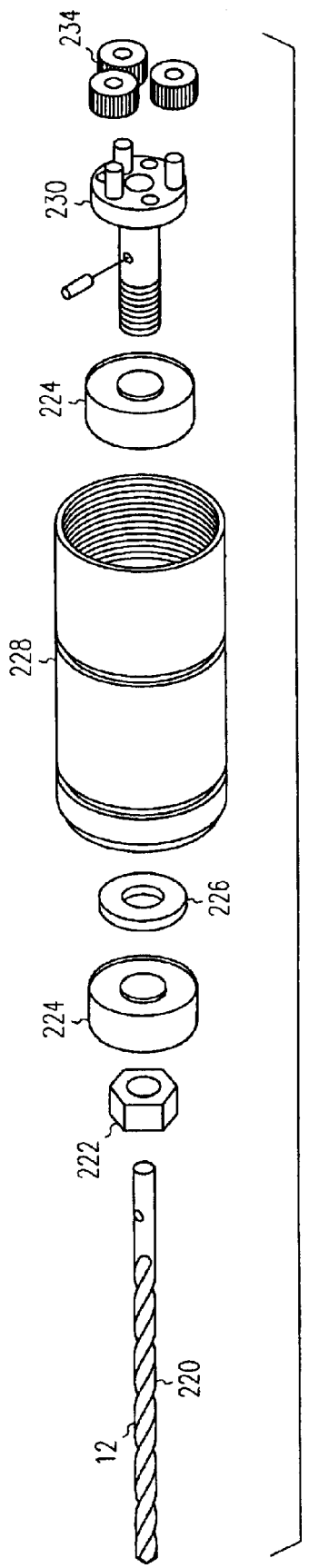
FIG. 20
FIG. 21B
FIG. 21A

CRANIAL DRILL WITH STERILE BARRIER

CROSS-REFERENCE TO RELATED APPLICATIONS

This Application claims the benefit under 35 U.S.C. 119(e) of U.S. Provisional Application No. 60/162,492 filed Oct. 29, 1999, incorporated herein by reference.

FIELD OF INVENTION

This invention relates to the field of medical devices, and more particularly to a MRI compatible disposable or reusable cranial drill, a sterile barrier for use with a cranial drills, and methods for their use.

BACKGROUND

Two issues with a medical device having several internal moving parts and mechanisms are cleaning and sterilization. These are especially troublesome if the device is to be used more for more than one procedure. Without disassembling, cleaning, and then re-assembling the device, it is difficult to do these steps adequately if the cleaning and sterilization steps are done at the hospital. Furthermore, it is difficult to design a device that can withstand the rigors of multiple sterilizations. Thus there is a need for a method and apparatus that can eliminate the need for resterilization.

An endoscope, a long instrument which is inserted in a body through the mouth or anus, is used for viewing internal structures of the body. A long tubular barrier has been used with an endoscope. A barrier for use with an endoscope has no features to accommodate rotating parts. There is a need for an apparatus and method for providing a sterile barrier for a device having rotating parts, such as a drill bit, for example. There is a further need for a method and apparatus that can eliminate the need for resterilization of a device such as a cranial drill or the like.

An additional issue associated with a cranial drill is the determination of a stopping point in the drilling process. It can take a long time to go through the process of drilling a small distance and stopping repeatedly to ascertain whether a necessary or desired depth has been reached. There is a need for an apparatus and method for automatically determining when to stop drilling or when the process is completed.

SUMMARY

The present invention provides cranial drills which are reusable or disposable. In one embodiment, the present invention provides a MR compatible cranial drill which is disposable. In one embodiment the present invention provides a MR compatible cranial drill which is reusable. The present invention in another embodiment provides a disposable sterile barrier for use with a cranial drill, which eliminates the need for re-sterilization. The sterile barrier may be used with a disposable cranial drill or a reusable cranial drill. When used with a disposable drill, the disposable drill becomes "re-sposable", i.e., the disposable drill may be used up to about five times and then discarded. When the sterile barrier is used, only the patient contacting portion of the drill, the drill bit, requires resterilization. The drill assembly itself is isolated from the patient with a sterile barrier. The barrier has an aperture that allows the drill bit to pass through the barrier while maintaining a seal around the circumference of the bit. In one embodiment, the barrier comprises a bag made of plastic. The drill assembly does not need to be designed to withstand several sterilizations. The novel aperture of the barrier allows a moving or active component of the drill assembly, i.e. the drill bit, to penetrate through the sterile barrier and function on both sides. In one embodiment, the sterile barrier is provided as a sterile kit in combination with a sterile drill bit pre-mounted in the aperture.

In one embodiment the present invention provides a cranial drill having an adjustable depth stop to allow the user to set a predetermined depth of penetration. The adjustable depth stop in one embodiment includes an adjustable screw. In another embodiment the depth stop includes a spring mounted clip shaped to mate with serrations provided on the exterior of a drill housing. In further embodiments the depth stop includes a push button ratchet or a collet lock.

DESCRIPTION OF FIGURES

FIG. 14A is the adjustment portion of a depth stop for use with a cranial drill bit in accordance with the present invention.

FIG. 14B is the adjustment portion of a depth stop for use with a cranial drill bit in accordance with the present invention.

FIG. 14C is the adjustment portion of a depth stop for use with a cranial drill bit in accordance with the present invention.

FIGS. 19A, 19B and 19C are perspective views and an exploded view of a cranial drill gear train assembly in accordance with the present invention.

FIG. 20 is an exploded view of a cranial drill output shaft assembly in accordance with the present invention.

FIGS. 21A and 21B are an exploded view and a perspective view of a cranial drill trigger assembly in accordance with the present invention.

DETAILED DESCRIPTION

Figure 1:
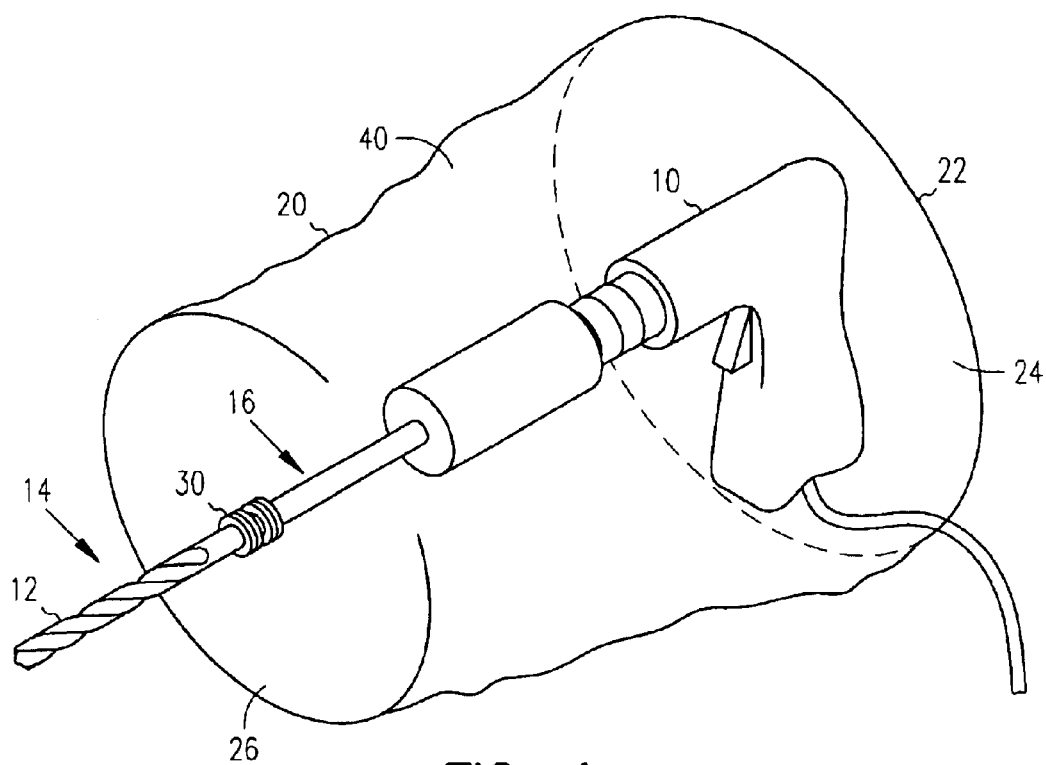
FIG. 1 is a perspective view of a cranial drill with a sterile barrier in accordance with the present invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

References in the detailed description to Figures without letter suffixes refer generally to any like numbered Figures with or without letter suffixes.

The leading digits of reference numbers appearing in the Figures generally corresponds to the Figure number in which that component is first introduced, such that the same reference numeral is used throughout to refer to an identical component which appears in multiple Figures.

The present invention provides cranial drills which are reusable or disposable. In one embodiment, the present invention provides a MR compatible cranial drill which is disposable. In one embodiment the present invention provides a MR compatible cranial drill which is reusable. The present invention in another embodiment provides a disposable sterile barrier for use with a cranial drill, which eliminates the need for re-sterilization. The sterile barrier may be used with a disposable cranial drill or a reusable cranial drill. When used with a disposable drill, the disposable drill becomes "re-sposable", i.e., the disposable drill may be used up to about five times and then discarded. When the sterile barrier is used, only the patient contacting portion of the drill, the drill bit, requires resterilization. The drill itself is isolated from the patient with a sterile barrier. The barrier has an aperture that allows the drill bit to pass through the barrier while maintaining a tight seal around the circumference of the bit. In one embodiment, the barrier comprises a bag made of plastic. The drill therefore does not need to be designed to withstand several resterilization cycles. The drill is capable of several re-uses, which will lower the overall cost of procedures utilizing a cranial drill. The novel aperture of the barrier allows a moving or active component of the drill to penetrate through the sterile barrier and function on both sides. In one embodiment, the sterile barrier is provided as a sterile kit in combination with a sterile drill bit pre-mounted in the aperture.

In one embodiment the present invention provides a cranial drill having an adjustable depth stop to allow the user to set a predetermined maximum allowable depth of penetration. The adjustable depth stop in one embodiment is an adjustable screw. In another embodiment the depth stop includes a spring mounted clip shaped to mate with serrations provided on the exterior of a drill bit. In further embodiments the depth stop includes a push button ratchet or a collet lock.

Figure 2:
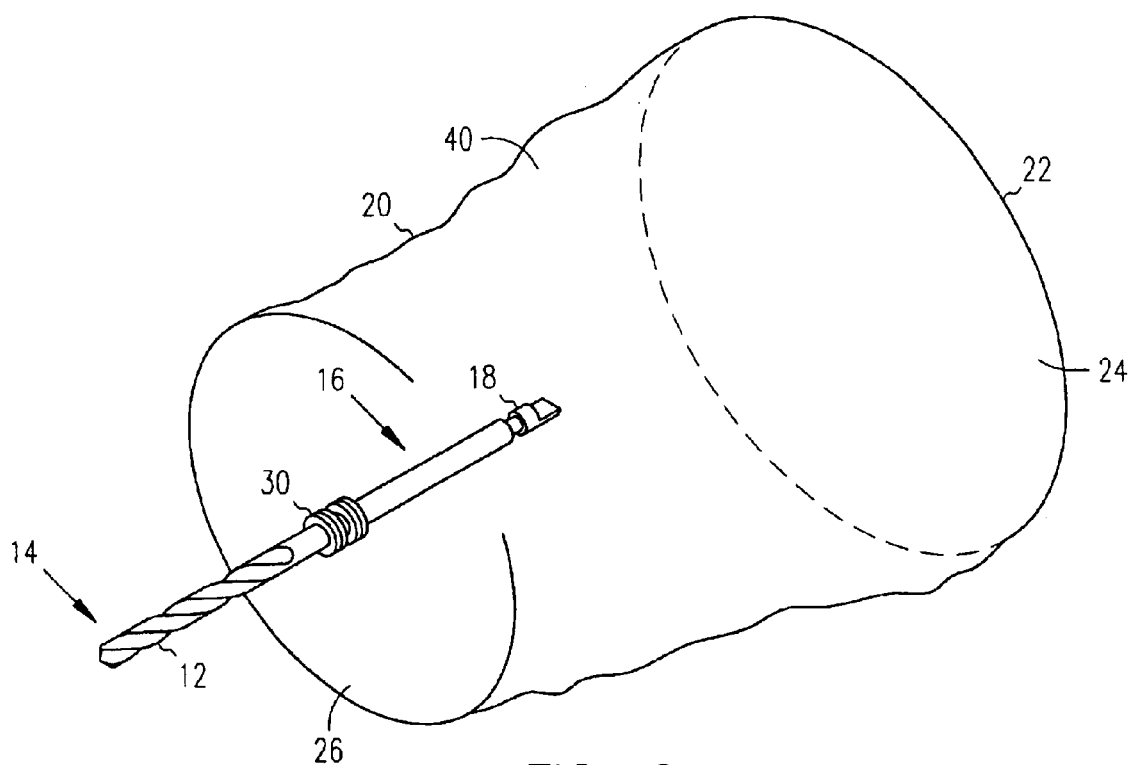
FIG. 2 is a perspective view of a drill bit and sterile barrier in accordance with the present invention.

At FIGS. 1 and 2, a cranial drill 10 associated with the sterile barrier 20 according to the present invention is shown. The sterile barrier 20 has a proximal end 22 with an opening 24 and a distal end 26. Sealed aperture 30 is provided in sterile barrier 20 and is located at its distal end 26. The aperture seals against the shaft of the drill bit 12, isolating the sterile side 14 from the nonsterile side 16. At FIG. 2 quick connect end 18 of drill bit 12 is shown. At FIG. 1, the drill bit 12 is shown connected to the drill cranial drill 10.

Cranial drill 10 is nonsterile. Cranial drill 10 is provided with a sterile barrier 20, eliminating the need for re-sterilization of the cranial drill 10. Only the patient contacting portion, the drill bit 12, requires sterilization and may be disposable. The cranial drill 10 is isolated from the patient by the sterile barrier 20. The sterile barrier 20 has a sealed aperture 30 that allows the drill bit 12 to pass through the sterile barrier 20 while maintaining a seal around the circumference of the bit 12. In one embodiment, the sterile barrier 20 comprises a bag 40 made of plastic. A nonlimiting example of a material of which the barrier may be made is polyethylene, although the bag 40 may be made of any material that can maintain sterililty. Bag 40 includes at least one layer, and may have multiple layers.

Figure 3:
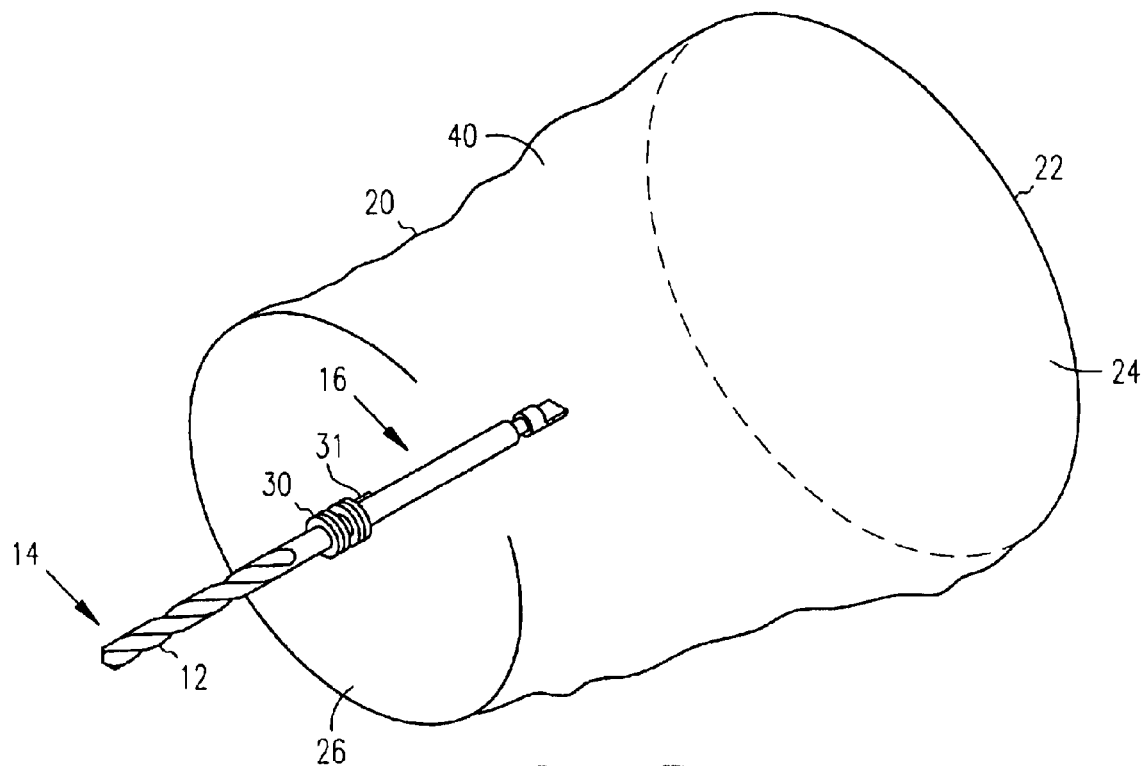
FIGS. 3–5 are perspective views of an alternative embodiment in accordance with the present invention.
Figure 4:
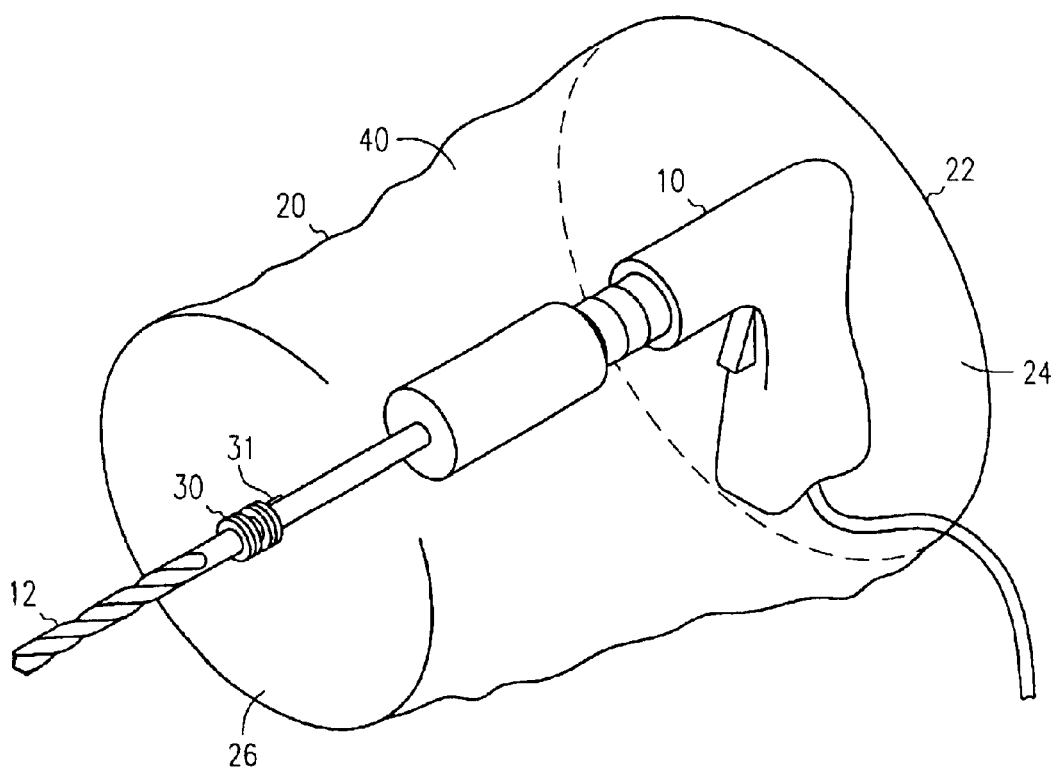
Figure 5:
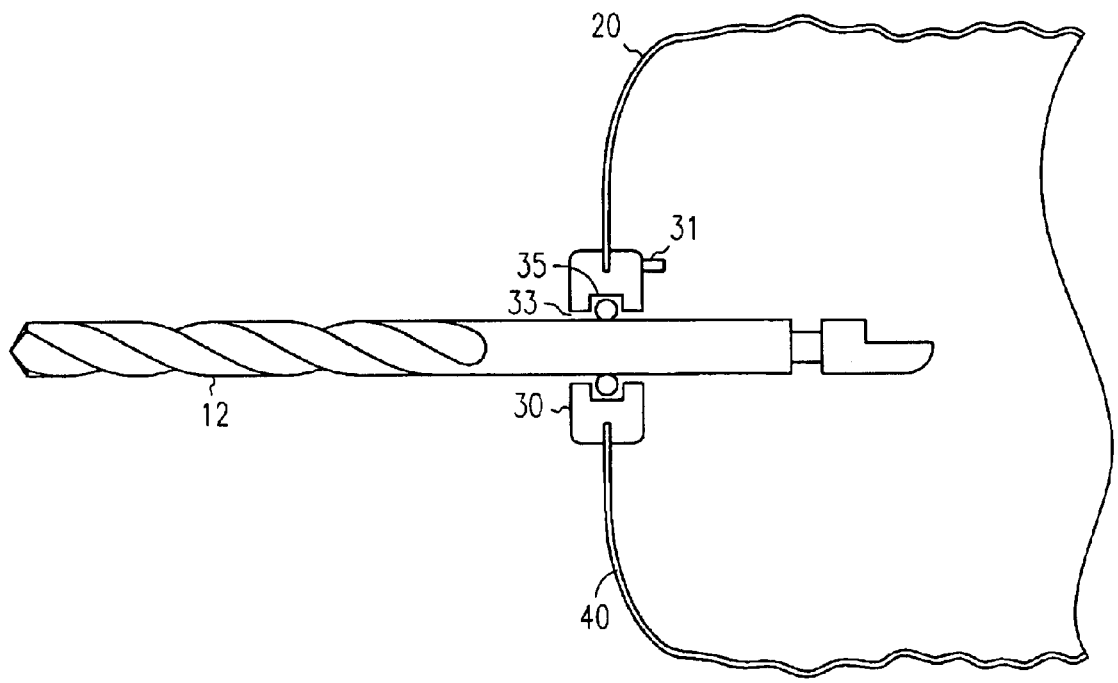

The cranial drill 10 does not need to be designed to withstand several resterilization cycles. The cranial drill 10 is capable of several re-uses, which will lower the overall cost of procedures utilizing a cranial drill. The novel aperture 30 of the barrier 20 allows a moving or active component of the drill to penetrate through the sterile barrier 20 and function on both sides of the barrier 30 while the sterile barrier is maintained. In one embodiment, the sterile barrier is provided as a sterile kit in combination with a sterile drill bit pre-mounted in the aperture. The range of sizes of the drill bit (either separate or pre-mounted) is from about 2–18 mm in diameter. The aperture is dimensioned to mate with the drill bit. The aperture in one embodiment includes an O-ring seal. Referring to FIGS. 3–5, the two rings around the shaft of the drill bit include an O-ring and an O-ring groove, which provides in one embodiment a liquid tight and hermetic seal around the drill bit. In another embodiment, the barrier includes a hook, loop or fastening means to anchor it to the drill, to prevent rotation of the barrier with the drill bit. As shown in FIGS. 3, 4 and 5, in one embodiment aperture 30 includes a pin 31 which fits into a hole 13 in the housing 11 of drill 10 to anchor barrier 20 to drill 10 and prevent rotation of barrier 20. Referring to FIG. 5, the O-ring 33 and O-ring groove 35 are shown.

Figure 6:
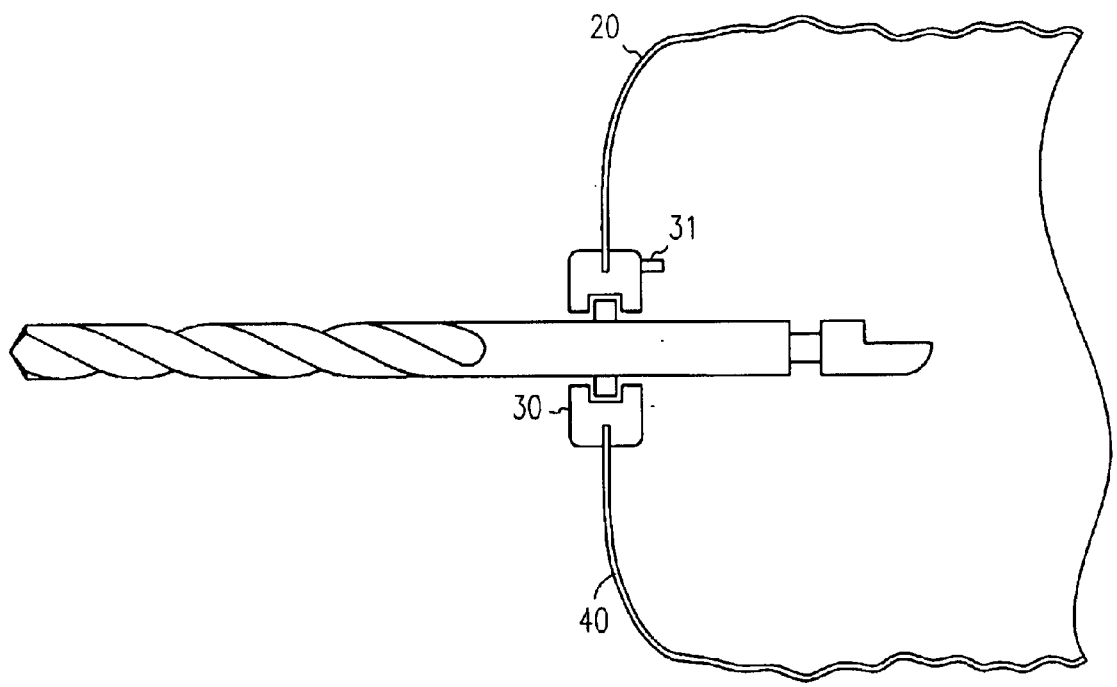
FIG. 6 is a perspective view of an alternative embodiment in accordance with the present invention.

In one embodiment, a silicone grease is provided between the drill bit and the seal. In a further alternative embodiment, the seal includes a perforatable membrane, as shown at FIG. 6. In another alternative embodiment, the aperture includes an additional bearing or bushing to hold the drill bit in the aperture allowing it to spin freely within the aperture.

The sterile barrier 30 of the present invention may therefore be used with any cranial drill having a removable sterile drill bit 12. In one embodiment, the cranial drill is a cranial drill capable of being used in close proximity to an MRI machine.

Figure 7:
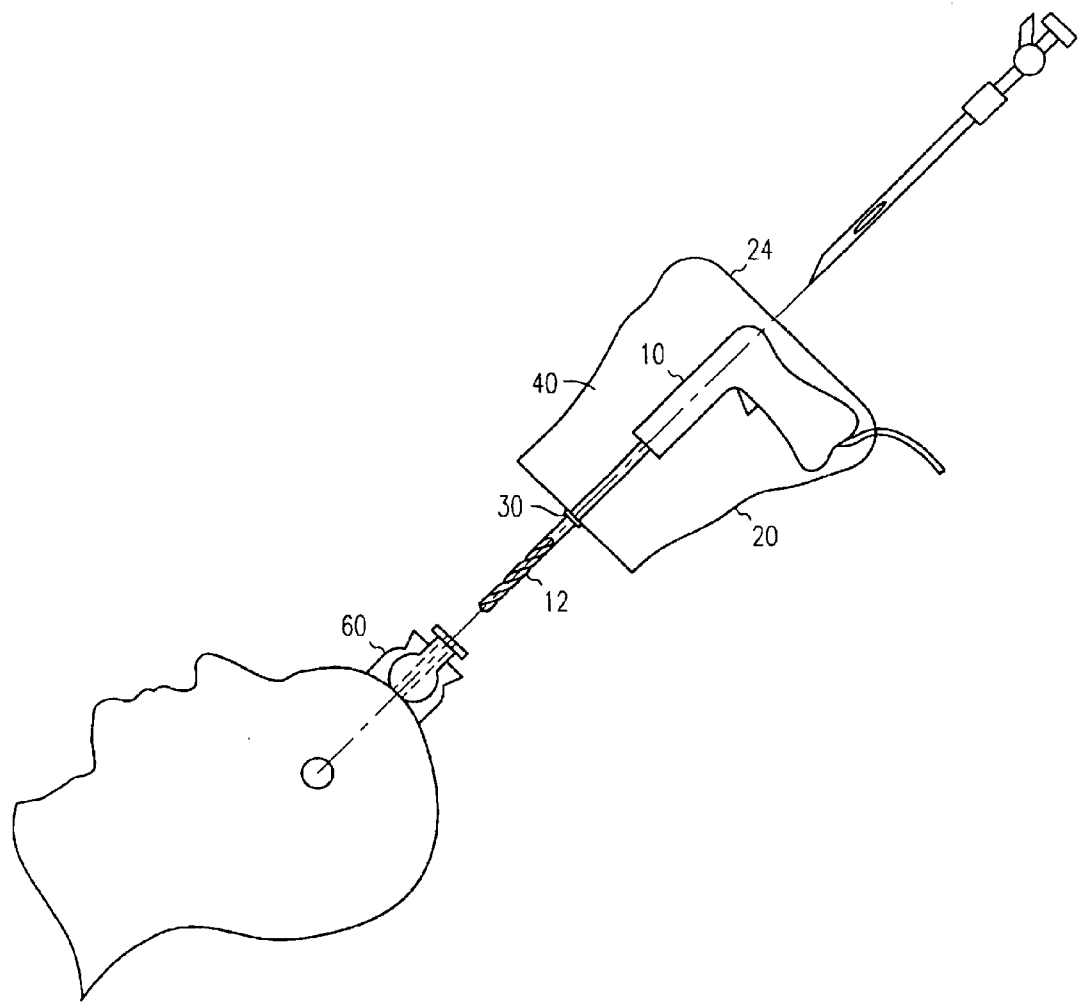
FIG. 7 is a side view of a cranial drill with sterile barrier in use in accordance with the present invention.

In current stereotactic procedures a burr hole is typically drilled in the skull in a location based on preoperative MRI or CT data. The hole may be as large as 14 mm in diameter even though the device requiring access may be several times smaller. The larger hole provides some compensation for movement of the brain after imaging and prior to insertion of a device, by allowing greater range of motion to hit the desired target. In one embodiment, the present invention provides a drill and trajectory method which provides a less invasive solution with greater accuracy. The less invasive nature of this method comes from the ability to drill directly along the trajectory path of the instrument requiring access. The accuracy comes from the ability to do alignment, drilling, and instrument insertion with real time imaging in a MRI or CT environment. Referring to FIG. 7, this is facilitated through the use of a skull mounted locking trajectory guide 60, such as that described in U.S. Pat. No. 5,993,463, incorporated herein by reference. Use of the lockable trajectory path assures target accuracy is maintained from drilling through instrument insertion.

In one embodiment, the present invention provides a method for providing access to a site within a body of a surgical patient, the method comprising providing a medical device comprising in combination a MRI compatible drill and a sterile drill bit, and providing a locking trajectory guide. The method includes mounting the trajectory guide on the patient's body, selecting a predetermined depth and adjusting the depth stop to the predetermined depth, advancing the medical device to the body and aligning it with the trajectory guide, utilizing the medical device to cause the sterile drill bit to penetrate the body the predetermined depth to which the depth stop is adjusted, and removing the sterile drill bit from the body. The method in one embodiment is used in MRI for any procedure, such as orthopaedic implantation, reconstructive surgery or the like.

In one embodiment, the medical device further comprises an adjustable depth stop whereby the depth of penetration of the drill bit is controlled. In a further embodiment, the medical device further comprises a sterile barrier having an interior portion, a proximal end, a distal end, a proximal opening at the proximal end and an opening at the distal end, the opening at the distal end further comprising a sealed aperture, the drill being insertable into the proximal opening, the sealed aperture constructed and arranged to seal around the drill bit such that the drill is enclosed in the interior portion of the sterile barrier and only a portion of the drill bit extends exteriorly of the barrier.

In one embodiment the present invention provides a method for providing access to a brain of a surgical patient. The method includes providing a medical device comprising in combination a MRI compatible cranial drill having a removable sterile drill bit and an adjustable depth stop whereby the depth of penetration of the drill bit is controlled; and a sterile barrier as described herein. The method includes providing a skull mounted locking trajectory guide, mounting the trajectory guide on the patient's skull, selecting a predetermined depth and adjusting the depth stop to the predetermined depth, advancing the medical device to the skull and aligning it with the trajectory guide, utilizing the medical device to cause the sterile drill bit to penetrate the skull the predetermined depth to which the depth stop is adjusted, and removing the sterile drill bit from the skull.

The use of the drill 10 in or in close proximity to the MRI requires special design considerations. More specifically, all component raw materials are required to be substantially non-magnetic to prevent inadvertent movement of the device as a result of the magnetic field in the environment. Although plastic is a logical choice for a number of components, non-magnetic metals such as aluminum, brass, titanium and stainless steel are also used throughout the assembly as dictated by design requirements.

Typically the use of smaller bit sizes are facilitated in neurological procedures through the use of hand cranked or manual drills. Any support or guidance comes from an external stereotactic frame. A drill 10 according to the present invention employs an air powered or compressed gas motor, and takes advantage of a skull mounted trajectory guide with real time imaging. This provides a more accurate and less invasive approach. This is preferred over an alternative to the special design constraints of a MRI compatible drill which would alter the procedure and require the patient to be removed from the magnet once trajectory alignment is achieved. A non-MRI compatible drill could then be used to gain access in another location such as an operating room. This would not only be a time consuming nuisance, but could create the risk of bumping the alignment stem and losing trajectory accuracy.

Figure 8:
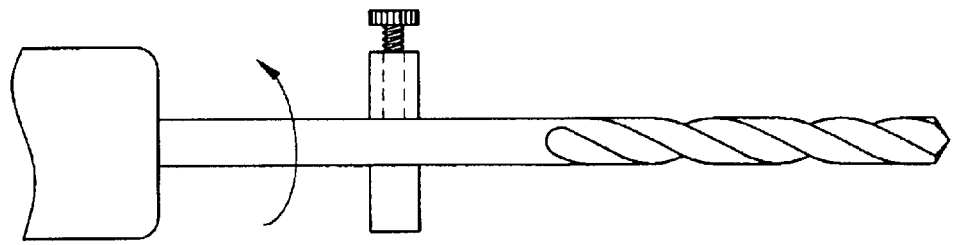
FIG. 8 is prior art depth stop.
Figure 9:
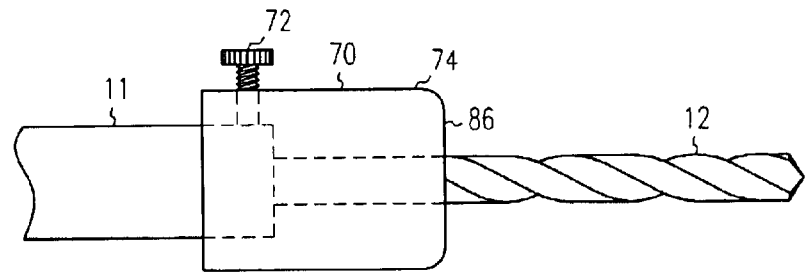
FIG. 9 is an adjustable depth stop for use with a cranial drill bit in accordance with the present invention.

The present invention in one embodiment includes an adjustable depth stop to allow a user to adjust the maximum allowable depth of penetration. FIG. 8 shows a prior art depth stop which requires the stop to rotate, which is undesirable. The depth stops of the present invention are stationary and do not rotate with the drill bit. Referring to FIGS. 9, 10, 11, 12, 13, 14A–B, 15, and 16A–B, embodiments of an integrated adjustable depth stop 70 is shown. The depth stop allows physicians to set the maximum allowable depth of penetration of the drill bit in cases where this is desirable. FIG. 9 shows an embodiment utilizing an adjustable screw. This depth stop is infinitely adjustable, i.e. adjustable to any depth within the range provided by the depth stop.

Figure 10:
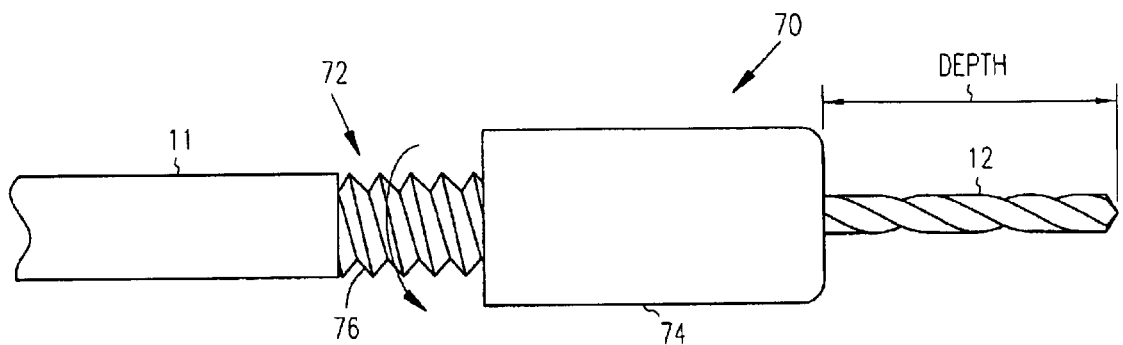
FIG. 10A is an adjustable depth stop for use with a cranial drill bit in accordance with the present invention.
FIG. 10B is an adjustable depth stop for use with a cranial drill bit in accordance with the present invention.
FIG. 10C is a portion of an adjustable depth stop for use with a cranial bit in accordance with the present invention.
Figure 10A:
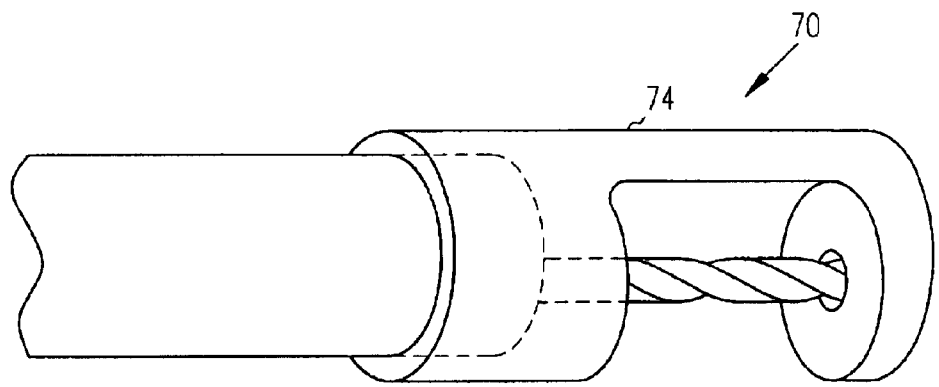
Figure 10B:
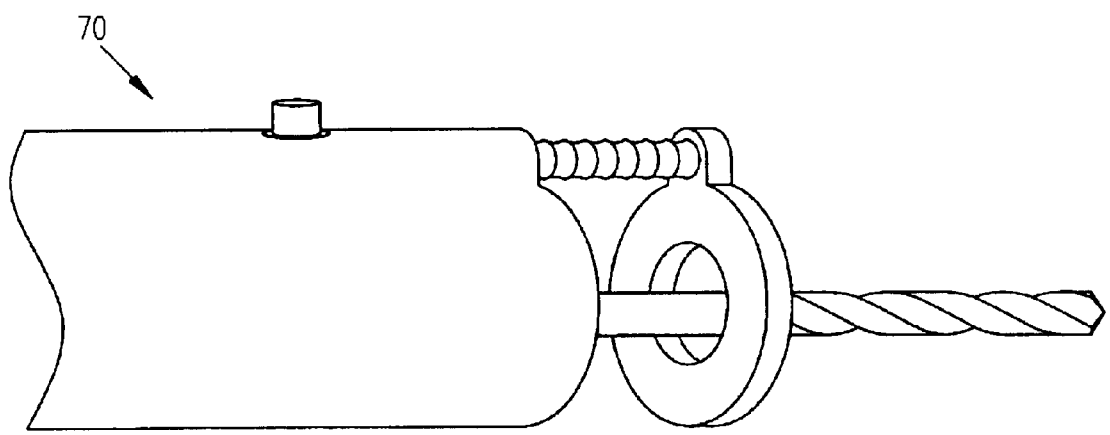
Figure 10C:
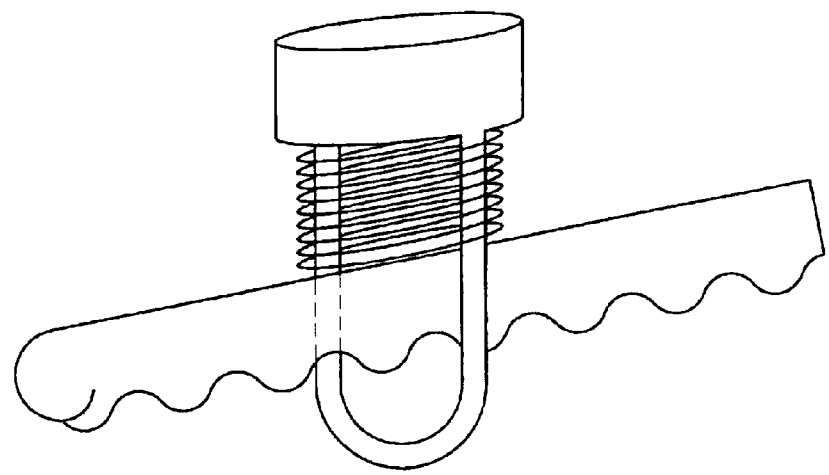
Figure 11:
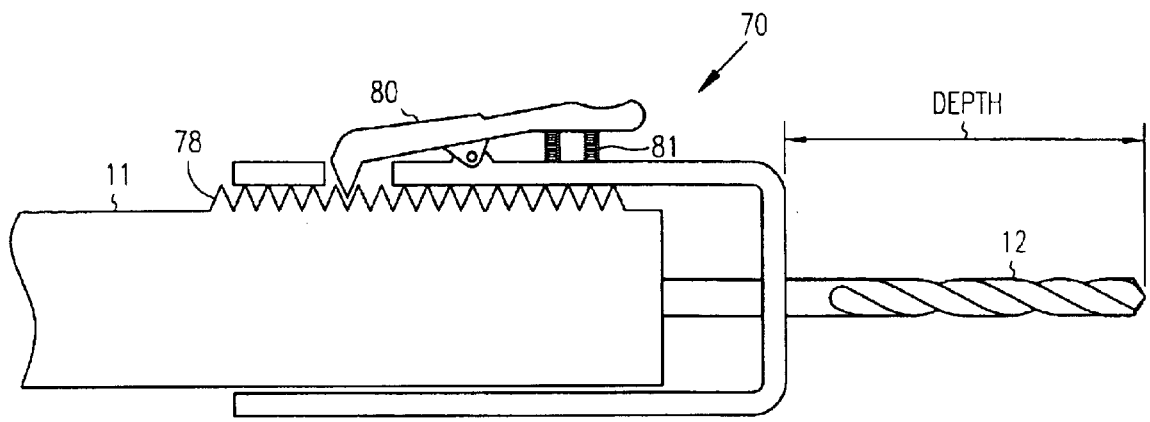
FIG. 11 is an adjustable depth stop for use with a cranial drill bit in accordance with the present invention.
Figure 12:
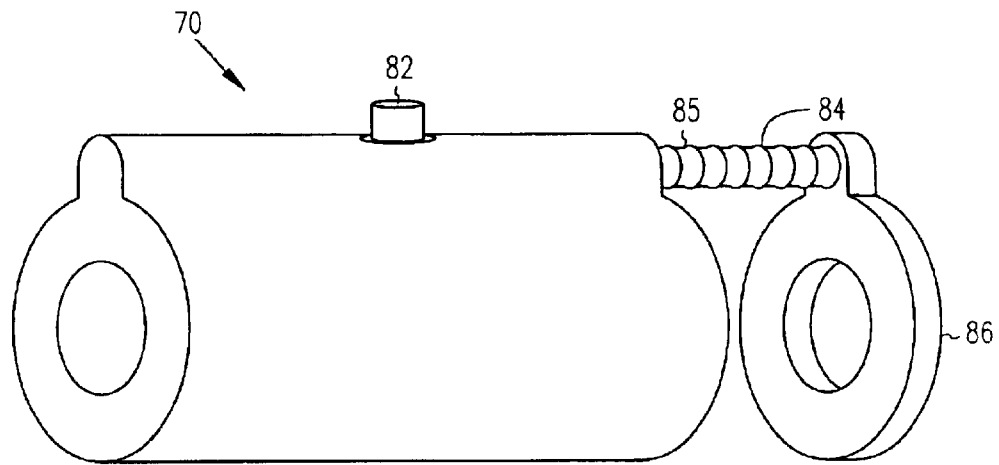
FIG. 12 is an adjustable depth stop for use with a cranial drill bit in accordance with the present invention.
Figure 13:
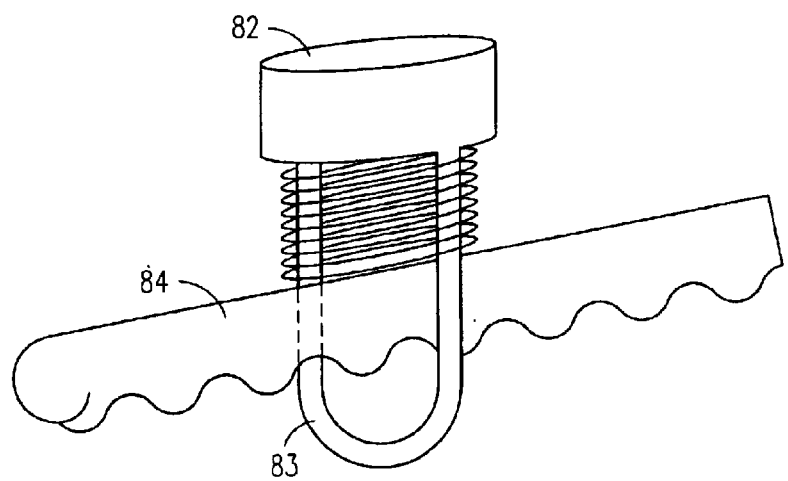
FIG. 13 is an enlarged view of the push button and its interaction with the ratchet as in FIG. 10.

In one embodiment shown at FIG. 10, the sleeve 74 of depth stop 70 has threads located on its interior surface which mate with the threads 76 on the housing 11 of the drill 10 to provide an infinitely adjustable depth stop. In one embodiment shown at FIG. 10A, housing 74 is partially open. In one embodiment shown at FIG. 11, a spring mounted clip 80 shaped to mate with serrations or teeth 78 provided on the exterior of a drill housing is provided. This embodiment is an incrementally adjustable depth stop, the various depths being determined by the serrations or teeth. In another embodiment shown at FIGS. 12–13, depth stop 70 includes a push button ratchet. Spring loaded push button 82 has a shaft which includes a ring 83. Ratchet 84 is incrementally adjusted by slots formed thereon. Pushing down on button 82 releases the ratchet 84 which may be moved by grasping and moving end ring 86. In this embodiment, the distal end of depth stop 70 is defined by end ring 86.

Figure 14D:
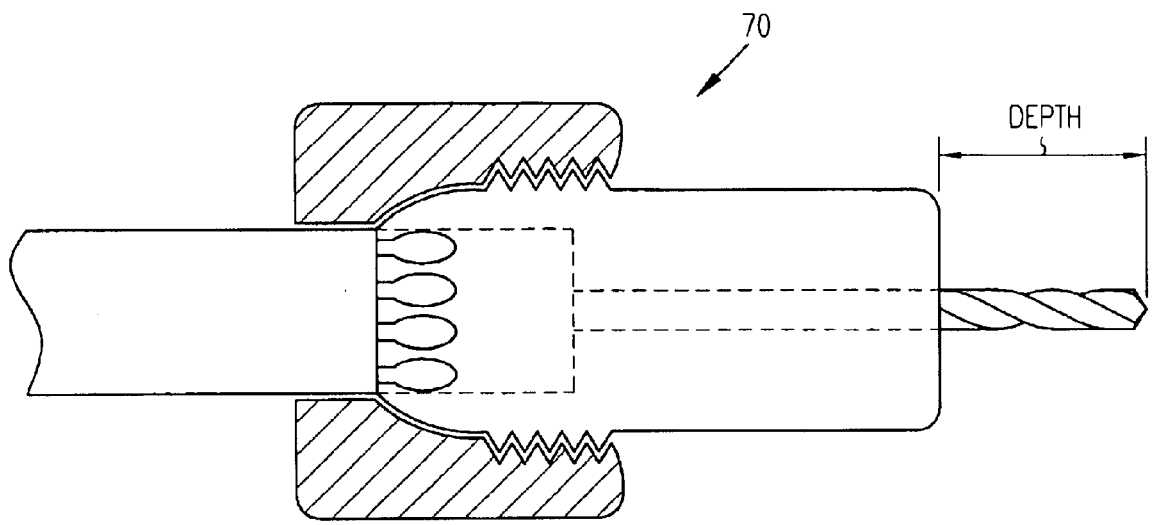
FIG. 14D is the adjustment portion of a depth stop for use with a cranial drill bit in accordance with the present invention.

In a still further embodiment shown at FIG. 14A an infinitely adjustable rotating locking means is shown. FIGS. 14B and 14C show this embodiment in axial cross section. Sleeve 74 of depth stop 70 and housing 11 of drill are elliptical, the sleeve of depth stop 74 fitting over housing 11. When the two long axes of the ellipses are aligned, the sleeve 74 slides freely along housing 11. Depth stop 70 may be telescoped to a place on the housing 11 corresponding with a desired depth. As elliptical sleeve 74 is rotated, the minor diameter of sleeve 74 wedges against the major outer diameter of the elliptical housing 11, causing sleeve 74 and housing 11 to lock together.

Figure 15:
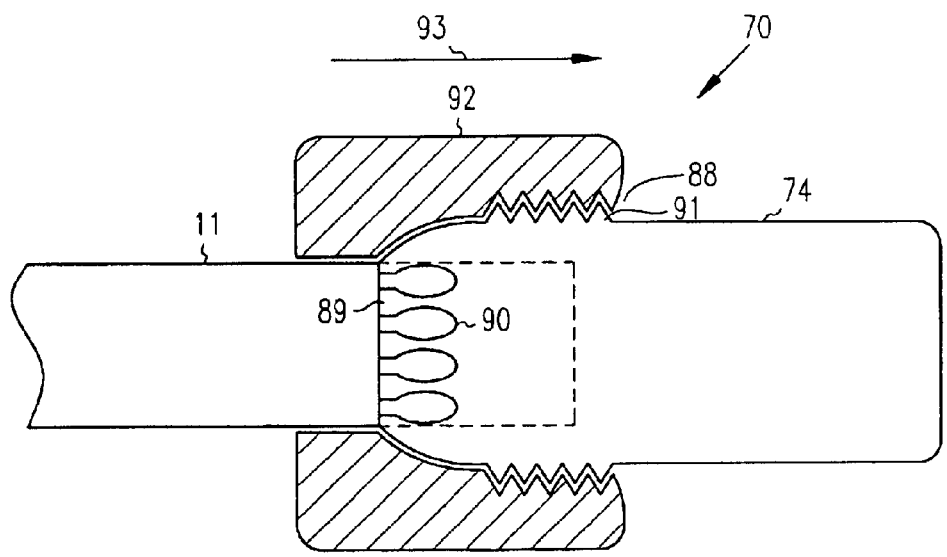
FIG. 15 is an adjustable depth stop for use with a cranial drill bit in accordance with the present invention.

In another embodiment shown at FIG. 15 an alternative depth stop 70 including a collet lock 88 is provided. Sleeve 74 of depth stop 70 is slidable along housing 11. Sleeve 74 has fingers 89 separated by slots 90 at its proximal end. Sleeve 74 has external threads 91. Locking nut 92 is screwed onto sleeve 74 in the direction indicated by arrow 93. As nut 92 is tightened, it wedges fingers 89 together and toward housing 11.

Figure 16A:
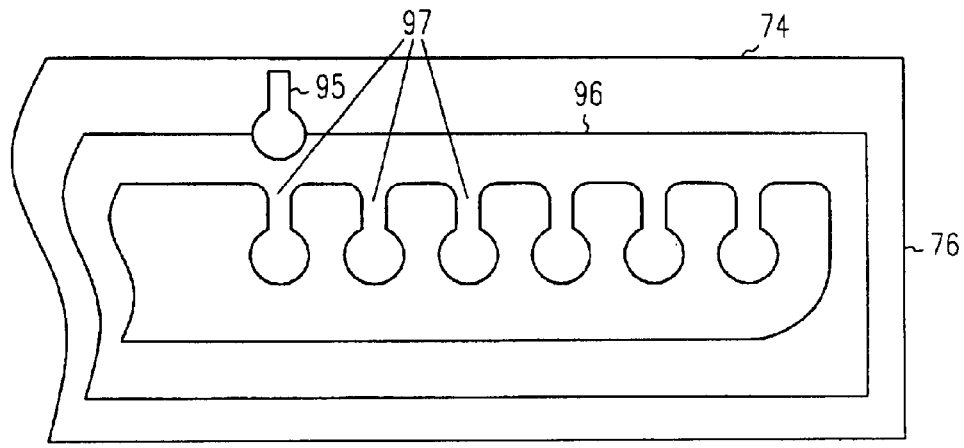
FIGS. 16A and 16B are views of an adjustable depth stop for use with a cranial drill bit in accordance with the present invention.
Figure 16B:
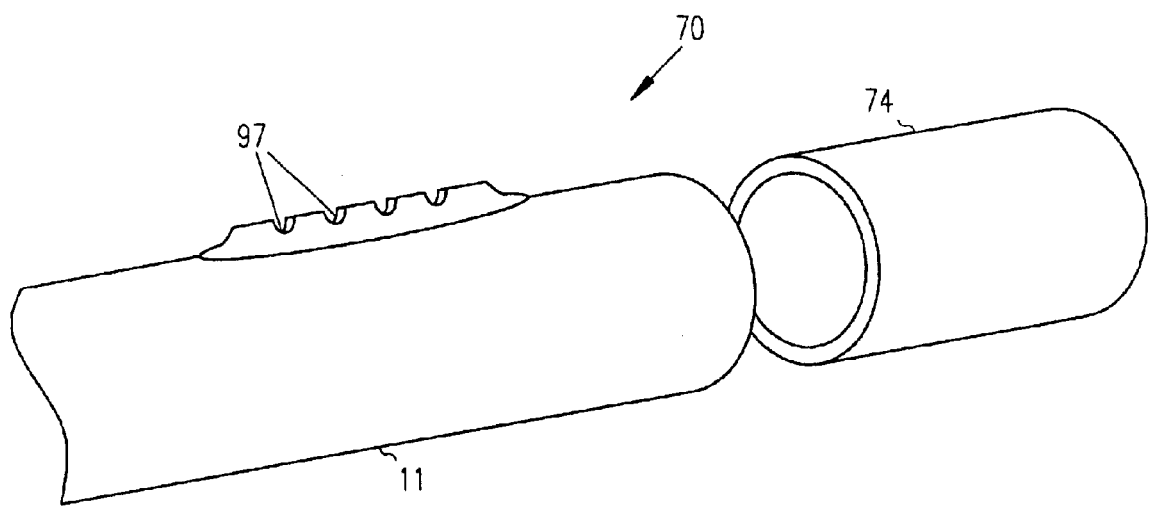
Figure 16C:
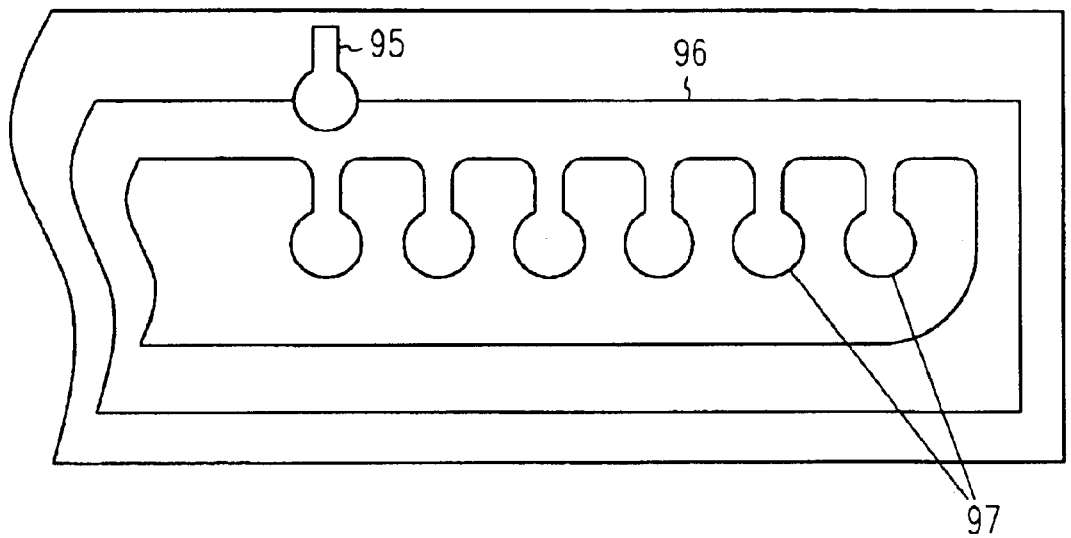
FIG. 16C is a view of an adjustable depth stop for use with a cranial drill bit in accordance with the present invention.
Figure 16D:
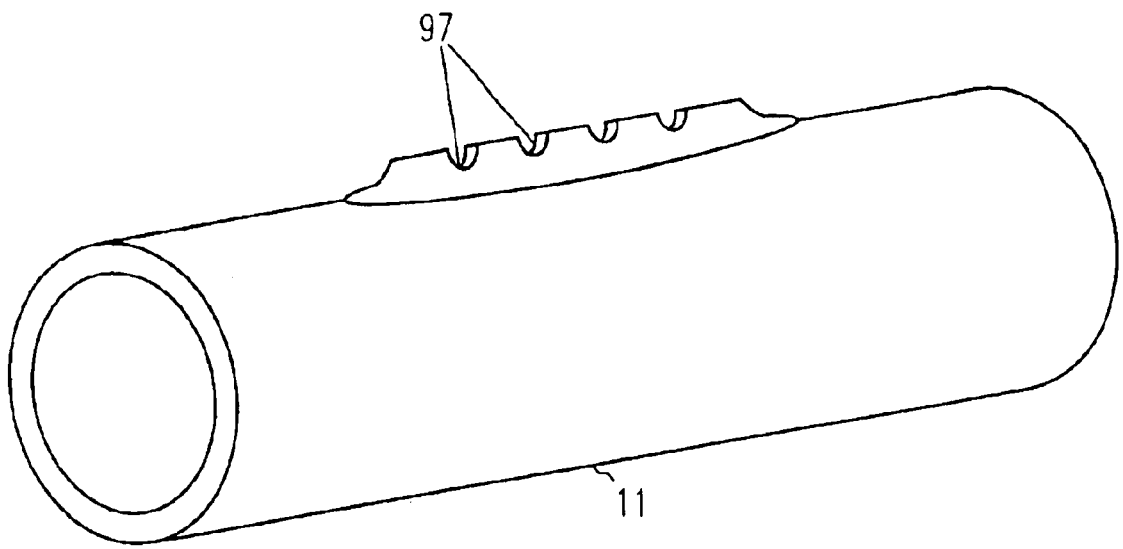
FIG. 16D is a view of an adjustable depth stop for use with a cranial drill bit in accordance with the present invention.

In a further embodiment shown at FIGS. 16A–B, sleeve 70 has a peg 95 on its inner diameter 96 which lines up with slots 97 located on the housing 11 of the drill 10, the slots or notches 97 being shaped to mate with the peg 95. In use, the peg is lined up with a slot corresponding to the desired depth. The sleeve 70 is rotated and the peg 95 snaps into place. The sleeve 70 is removed by rotating the sleeve in an opposite direction and snapping the peg 95 out of the slot 97.

In use, the depth stop limits the penetration of the drill bit in a patient's skull. The distal end 86 of the depth stop 70 contacts the patient's skull or the trajectory guide (as shown at 60 in FIG. 3) when the maximum depth is reached.

Referring to FIGS. 17, 18A–C, 19A–C, 20, 21A–B, and 22–35, in one embodiment a cranial drill according to the present invention is designed for use with Image-Guided Neurologic's Navigus Trajectory system. The Navigus establishes a defined path to a target located in the patient's skull. The cranial drill utilizes the Navigus' ball stem as a guide (in the same manner in which a drill guide bushing directs the path of a drill bit). Utilization of this system allows the surgeon to bore a minimum sized operating hole. The surgeon is also assured that the hole is in the direct line of the target. The drill can also be employed without the use of the Navigus.

Referring to FIGS. 18A–C and 22–26, the motor 100 of the cranial drill is based on vane motor technology. A rotor 112 is contained inside a sleeve 116. The rotor 112 has five vanes 114 which are allowed to slide in and out as the rotor rotates. The rotor 112 and vanes 114 are eccentric with respect to the flow sleeve. Air or Nitrogen is introduced at the point where the rotor 112 is closest to the flow sleeve. This requires the least volume of air/nitrogen consumption. The nitrogen is exhausted when the rotor 112 is furthest from the flow sleeve 116. This puts the least amount of back pressure on the motor. Nitrogen is exhausted quicker than it can be introduced. This constant intake and exhaust causes the rotor 112 and vane 114 assembly to rotate.

In one embodiment, the rotor 112 is constructed of brass due to its large density value. The high density will maximize the inertia of the rotor 112, which will in turn yield a higher output torque than that of a less dense material. The remaining parts in the motor 100 assembly are of various plastics to allow MR compatibility.

In a perfect motor assembly, ball bearings would aid in reducing friction in the system. The cranial drill motor 100 is unable to utilize ball bearings. All of the current metal ball bearings are not MR compatible and any available plastic ball bearings are not capable of handling the motor's speed (about 30,000 RPM). Therefore, the rotor 112 shaft surface spins within tightly toleranced holes, also known as a sleeve or sleeve bearing. There is a trade off between friction and sealing. Any area that allows nitrogen to escape creates loss in the motor efficiency, while a nitrogen tight assembly would not allow the rotor shaft to spin The cranial drill motor 100 provides a balance of minimal friction and leakage.

Figure 17:
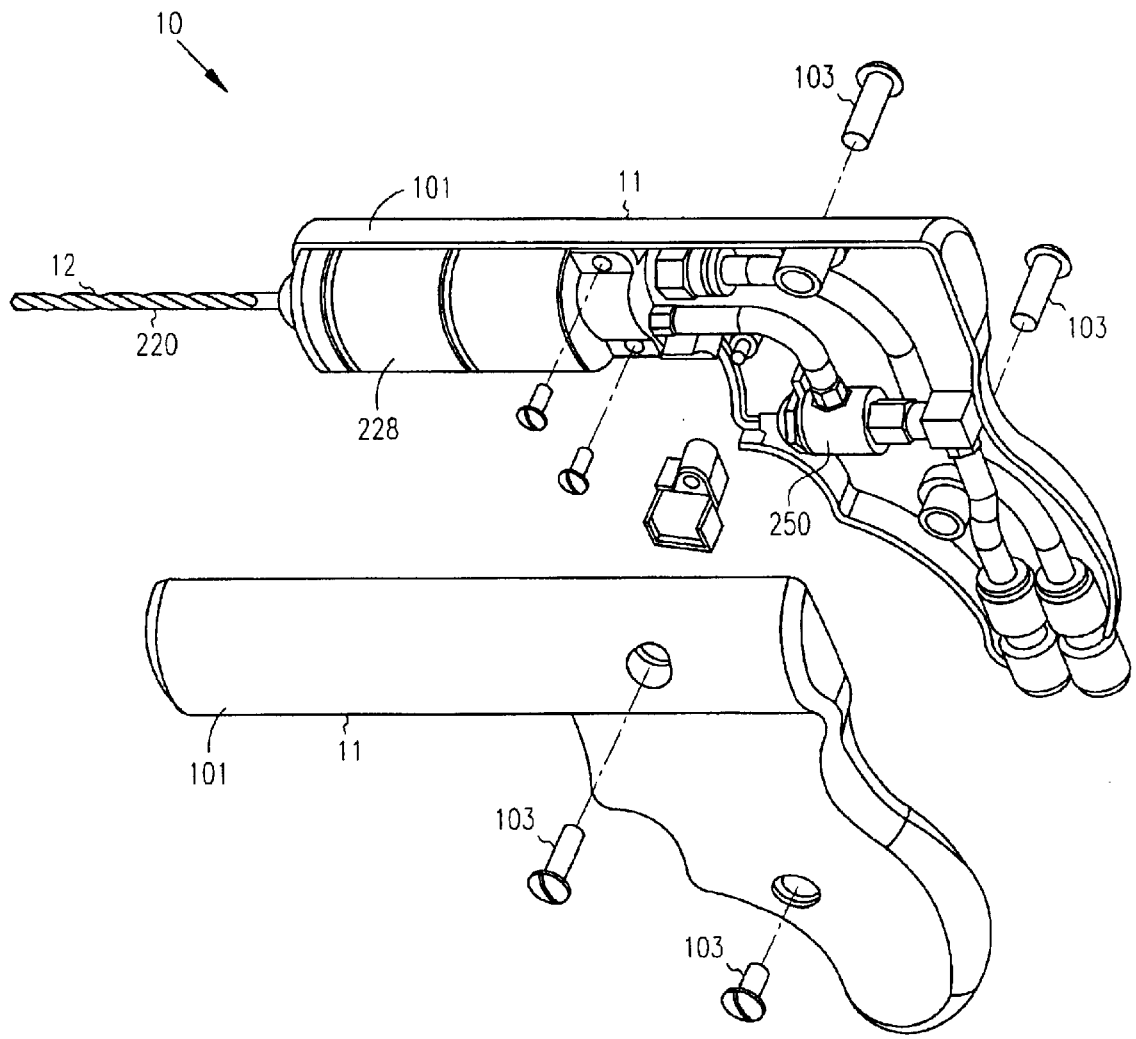
FIG. 17 is a partially exploded view of a cranial drill in accordance with the present invention.
Figure 18A:
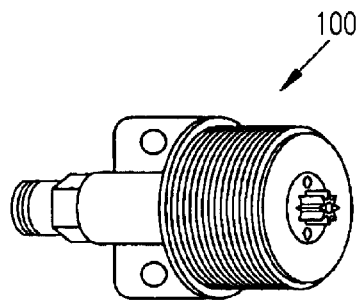
FIGS. 18A, 18B and 18C are perspective views and an exploded view of a cranial drill motor assembly in accordance with the present invention.
Figure 18B:
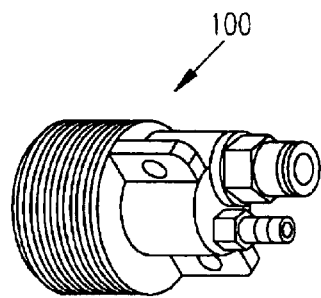
Figure 18C:
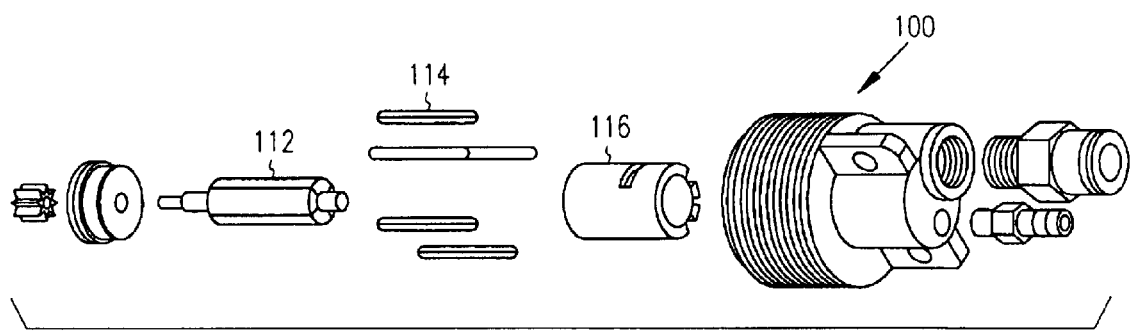

FIG. 17 shows a cranial drill assembly in accordance with one embodiment of the present invention. Exterior housing 101 has two parts joined together by fastening means such as screws 103. In one embodiment, exterior housing 101 may be of two parts snap fit together, or permanently sealed as by adhesive or the like.

In order to convert the high motor speed into a usable torque, the cranial drill utilizes a planetary gear train 200, shown at FIGS. 19A–C. The gear ratio is 49:1, This is done by utilizing two "in-line" 7:1 planetary gear trains. The sun 210, planet 212, and ring gears 214 are all plastic, brass or other nonmagnetic material for MR compatibility.

Cranial drill trigger assembly 250, shown at FIG. 17 and FIGS. 21A–B, includes fittings 252, two-way valve 254 and fitting 256.

Figure 22:
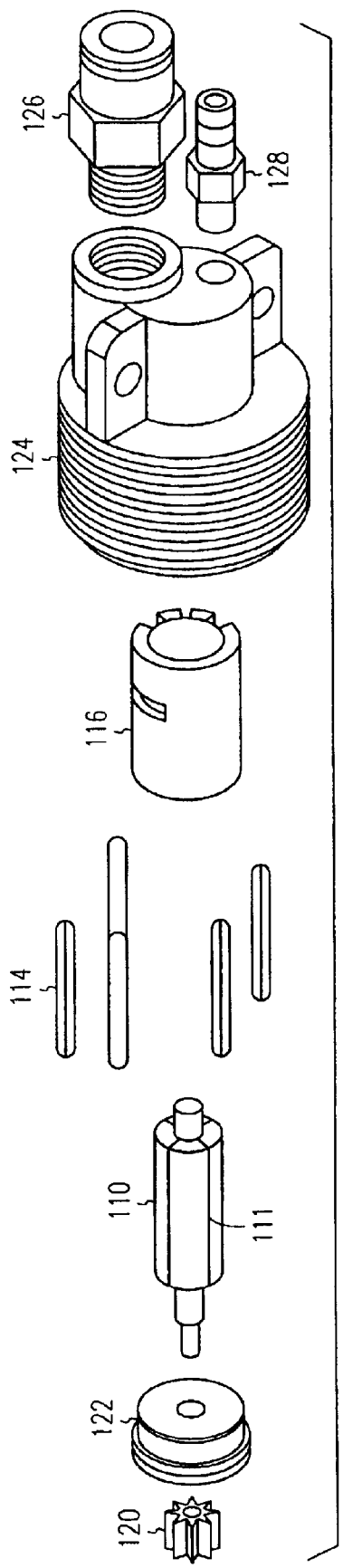
FIG. 22 is an exploded view of a cranial drill motor assembly in accordance with the present invention.
Figure 23:
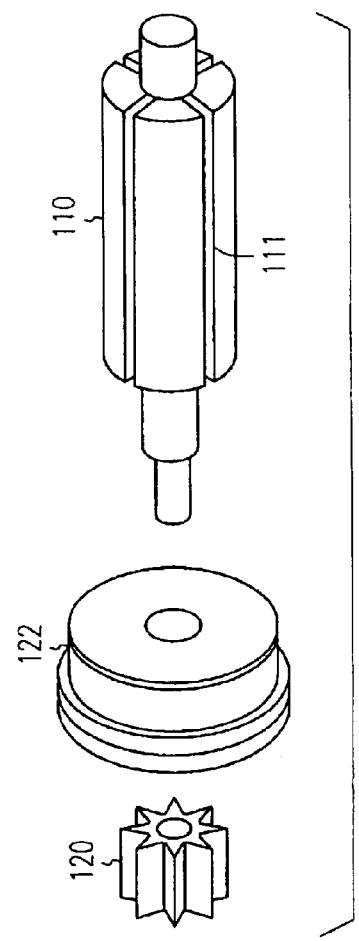
FIGS. 23–26 are perspective views of assembly of the cranial drill motor assembly in accordance with the present invention.
Figure 24:
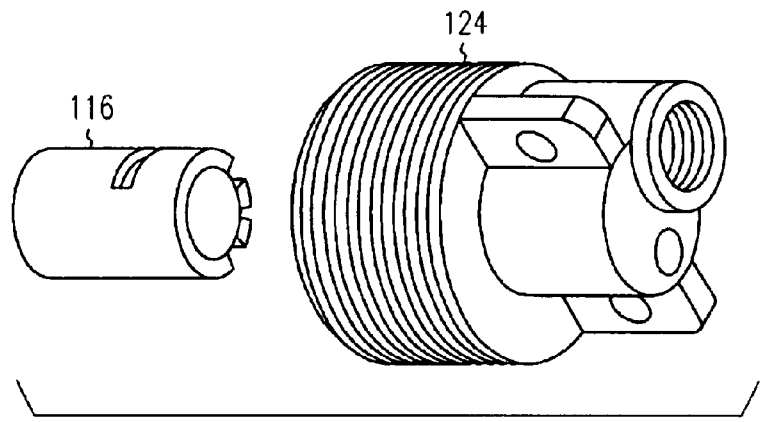
Figure 25:
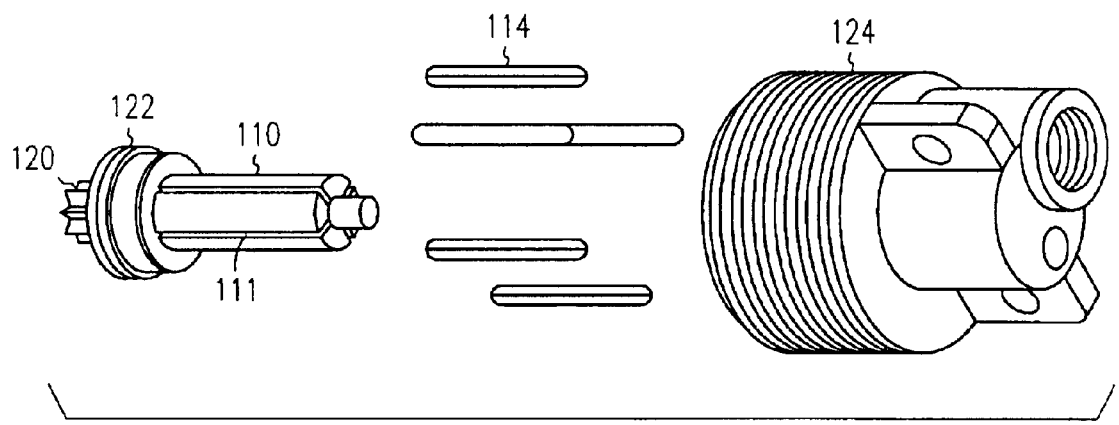
Figure 26:
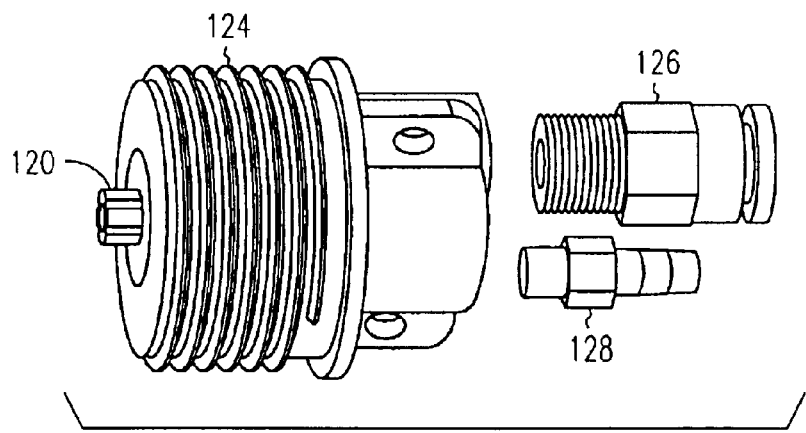

Referring now to FIGS. 22–26, the cranial drill motor assembly 100 is shown. FIG. 22 shows an exploded view. The motor comprises (from left to right) the sun gear 120, motor bearing 122, rotor 110, vanes (5) 114, flow cylinder 116, back housing 124, exhaust fitting 126, and inlet fitting 128.

The drill motor rotor 110 is inserted through drill motor bearing 122. Motor sun gear 120 is pressed onto the drill motor rotor 110. The rotor gear assembly is checked to ensure that it spins freely within the bearing 122.

The motor flow cylinder 116 is inserted into the back motor housing 124. There is a keying "half cylinder" in the back motor housing which mates with the flow cylinder keying feature. This keying feature will prevent the flow cylinder from rotating. If the flow cylinder is inserted backwards or if the keying features are not aligned, it will not seat flush to the back wall of the back motor housing 124.

The five cranial drill motor vanes 114 are placed into the grooves 111 in the drill motor rotor 110. The rotor assembly and vanes are inserted through the flow cylinder 116, while ensuring that all vanes 114 are seated in their respective grooves 111. Once the rotor assembly is inserted to the position where the motor bearing begins to make contact, the motor bearing is screwed into the back motor housing.

The inlet and exhaust fittings 126, 128 are secured to the back motor housing. The exhaust fitting is much larger than the inlet fitting.

Figure 27:
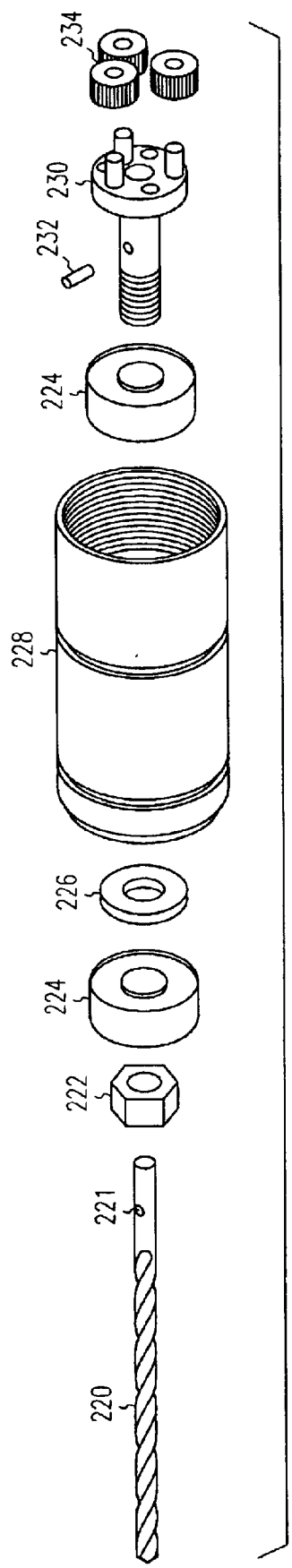
FIG. 27 is an exploded view of the output drive shaft assembly of a cranial drill in accordance with the present invention.
Figure 28:
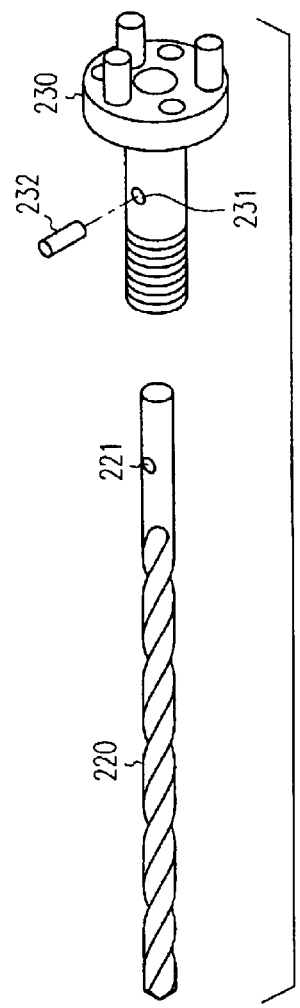
FIGS. 28–35 are perspective views of assembly of the output drive shaft, gear train and motor assembly of a cranial drill in accordance with the present invention.

Referring to FIGS. 27–35, the output drive shaft, gear train and motor assembly are shown. FIG. 27 shows an exploded view of the output drive shaft assembly. The output drive shaft assembly includes a drill bit 12 (also referred to as twist drill 220), nylon nut 222, plastic ball bearings (2) 224, nylon washer 226, front motor housing 228, drive shaft 230, stainless steel dowel pin 232, and planet gears 234.

The twist drill 220 and the dowel pin 232 are located. The twist drill 220 has a hole 221 towards the end away from the flutes. One side of the hole 221 is a slip fit for the dowel pin 232. The dowel pin 232 is inserted into each hole side to locate the slip fit side. The side which is the slip is identified. The dowel pin 232 is not inserted immediately. The twist drill 220 is inserted into the drive shaft 230, and turned until the hole 231 in the drive shaft 230 and the hole 221 in the twist drill 220 are aligned. The dowel pin 232 is then inserted into the hole 221 of the twist drill.

Figure 29:
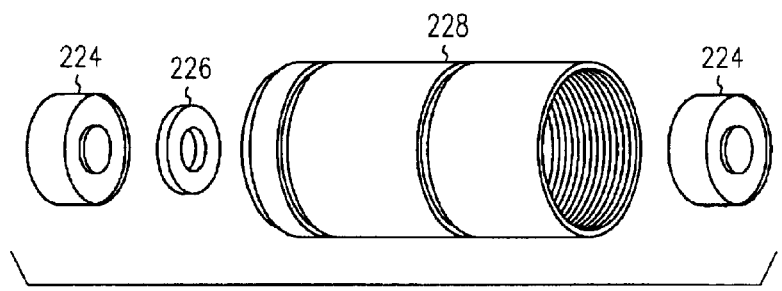

Referring to FIG. 29, one of the two plastic ball bearings 224 is inserted in through the deep hole pocket of the front motor housing 228. The bearing is inserted until it fully seats to the counterbored hole shoulder.

The nylon washer 226 is placed from the front of the motor housing onto the bearing which was previously placed. The second plastic ball bearing is inserted into the counterbored hole in the front of the motor housing. The plastic ball bearing is pressed in until it is fully seated.

Figure 30:
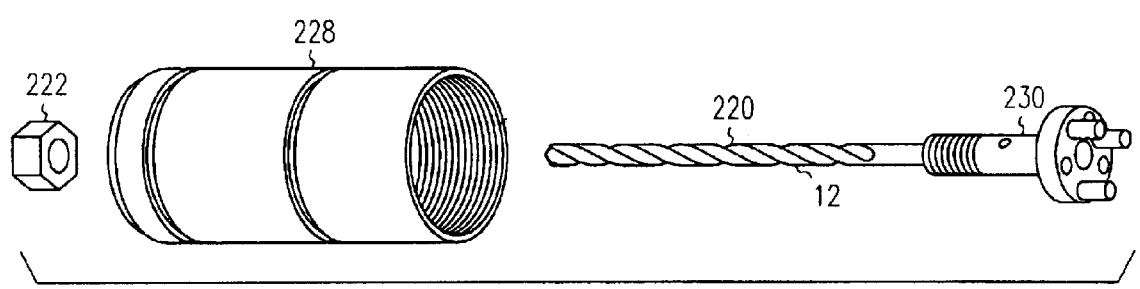
Figure 31:
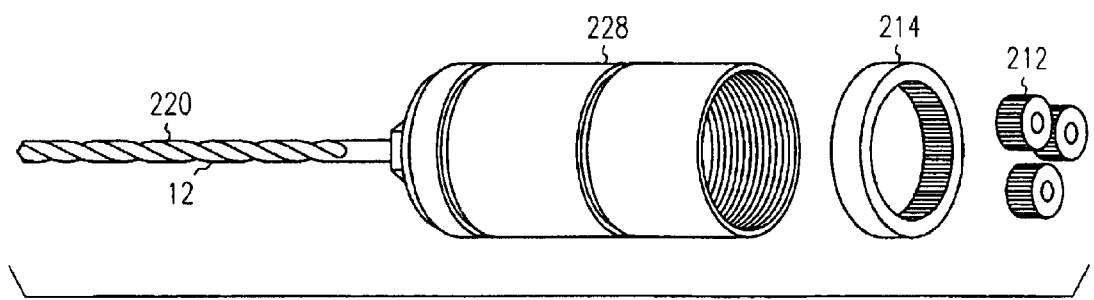
Figure 32:
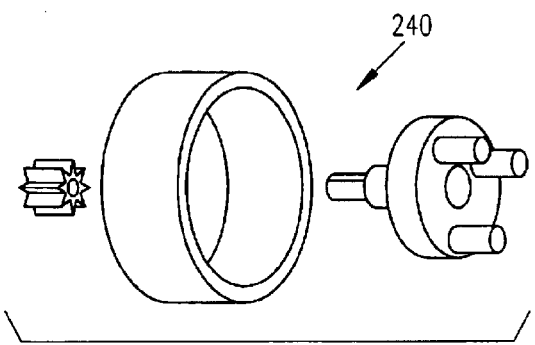
Figure 33:
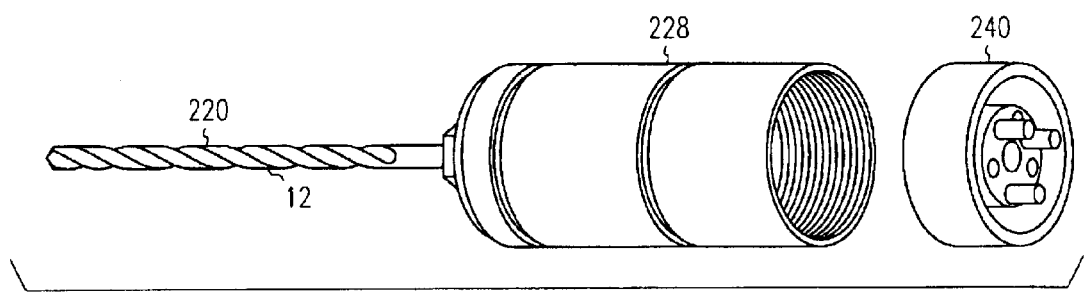
Figure 34:
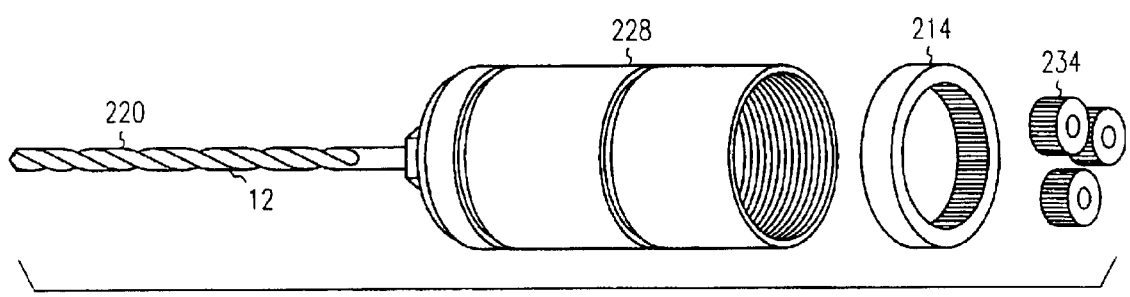
Figure 35:
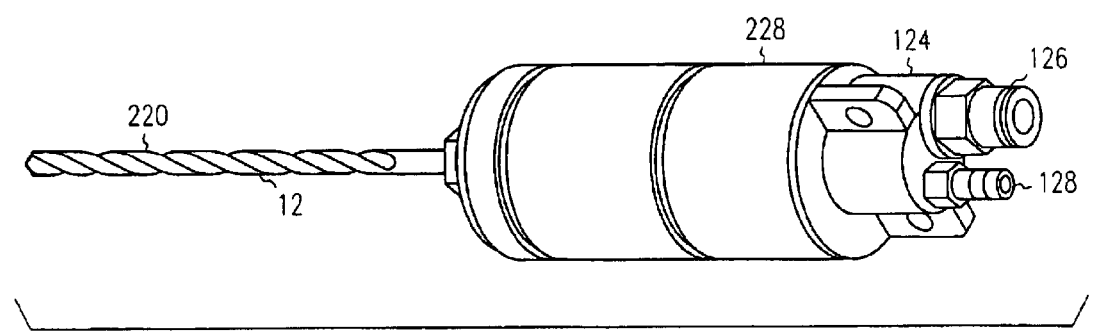

Referring to FIG. 30, the assembled drive shaft/drill bit sub-assembly is inserted through the two plastic bearings and nylon washer. The nylon nut 222 is tightened on to the drill drive shaft 230.

All of the spur gears (with the exception of the spur gear on the motor assembly), internal gears, drill gear bearing spacer, and the intermediate drive shaft are placed into a plastic bag.

One of the two internal gears is inserted into the rear of the back motor housing 228, while ensuring that the internal gear seats to the furthest shoulder. Three (3) spur gears 234 are placed onto the studs protruding from the drill drive shaft. Minor rotation of the drive shaft/drill bit assembly may be required to position the gears correctly.

The intermediate gear drive train 240 is assembled. The intermediate drive shaft, drill gear bearing spacer, and a motor sun gear are located. The "keyed" shaft of the intermediate drive shaft is inserted through the gear bearing spacer. The three (3) studs on the intermediate drive shaft should reside in the deeper side of the pocket on the gear bearing spacer. With the shaft extending through the gear bearing spacer, the sun gear is pressed onto the shaft until the gear seats flush to the shoulder.

The intermediate gear drive train assembly 240 is inserted into the front motor housing. The second internal gear 250 is inserted into the front motor housing 228. The three (3) remaining planet gears 234 are inserted onto the exposed studs of the intermediate drive shaft 230. The motor assembly 100 is assembled to the output drive shaft assembly 200.

It is understood that the above description is intended to be illustrative and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A medical device comprising:
    a drill assembly comprising in combination:
        a MRI compatible cranial drill; and
        a drill bit; and
    a sterile barrier having an interior portion, a proximal end, a distal end, a proximal opening at the proximal end and an opening at the distal end, the opening at the distal end further comprising a sealed aperture, the drill being insertable into the proximal opening, the sealed aperture constructed and arranged to seal around the drill bit such that the drill assembly is enclosed in the interior portion of the sterile barrier and only a portion of the drill bit extends beyond the barrier into a sterile field.

2. The medical device of claim 1 wherein the sterile barrier comprises a bag made of plastic.

3. The medical device of claim 1 wherein the drill bit is sterile and the drill is nonsterile.

4. The medical device of claim 1 wherein the MRI compatible cranial drill is an air or compressed gas powered bone drill.

5. The medical device of claim 4 wherein the drill is disposable.

6. The medical device of claim 4 wherein the drill is re-sterilizable and reusable.

7. The medical device of claim 1 or claim 4, further comprising a skull mounted locking trajectory guide.

8. The medical device of claim 1 or claim 4 further comprising a MRI compatible adjustable depth stop whereby the depth of penetration of the drill is controlled.

9. The medical device of claim 8 wherein the depth stop includes at least two depth positions.

10. The medical device of claim 8 wherein the depth stop does not rotate with the drill bit.

11. The medical device of claim 8 wherein the adjustable depth stop is constructed and arranged to provide a first predetermined depth.

12. The medical device of claim 1 wherein the adjustable depth stop is constructed and arranged to provide at least one additional predetermined depth.

13. The medical device of claim 8 wherein the adjustable depth stop includes an adjustable screw.

14. The medical device of claim 8 wherein the adjustable depth stop includes a spring mounted clip having teeth shaped to mate with a plurality of serrations located on the drill bit, each serration corresponding to a predetermined depth and indicating relative depth stop position.

15. The medical device of claim 8 wherein the adjustable depth stop includes a button ratchet.

16. The medical device of claim 8 wherein the adjustable depth stop includes a collet lock.

17. The medical device of claim 1 wherein the drill bit is sterilizable and reusable.

18. The medical device of claim 1 wherein the drill bit is disposable.

19. The medical device of claim 1 at least a portion of which is made nonmagnetic plastic.

20. A sterile barrier having an interior portion, a proximal end, a distal end, a proximal opening at the proximal end and an opening at the distal end, the opening at the distal end further comprising a sealed aperture, the sterile barrier constructed and arranged to enclose a medical device that includes a drill, such that the drill is enclosed in the interior portion of the sterile barrier and only a portion of a drill bit extends exteriorly of the barrier, and wherein the aperture includes a member that is sized and shaped to engage the medical device.

21. A method for providing access to a site within a body of a surgical patient, the method comprising:
    providing a medical device comprising in combination:
        a MRI compatible drill;
        a sterile drill bit; and
        a sterile barrier having an interior portion, a proximal end, a distal end, a proximal opening at the proximal end and an opening at the distal end, the opening at the distal end further comprising a sealed aperture, the drill being insertable into the proximal opening, the sealed aperture constructed and arranged to seal around the drill bit such that the drill is enclosed in the interior portion of the sterile barrier and only a portion of the drill bit extends exteriorly of the barrier;
    providing a locking trajectory guide;
    mounting the trajectory guide on the patient's body;
    selecting a predetermined depth and adjusting a depth stop to the predetermined depth;
    advancing the medical device to the body and aligning it with the trajectory guide;
    utilizing the medical device to cause the sterile drill bit to penetrate the body the predetermined depth to which the depth stop is adjusted; and
    removing the sterile drill bit from the body.

22. The method of claim 21 wherein the medical device further comprises an adjustable depth stop whereby the depth of penetration of the drill bit is controlled.

23. A method for providing access to a brain of a surgical patient, the method comprising:
providing a medical device comprising in combination:
a MRI compatible cranial drill having a removable sterile drill bit and an adjustable depth stop whereby the depth of penetration of the drill bit is controlled; and
a sterile barrier having an interior portion, a proximal end, a distal end, a proximal opening at the proximal end and an opening at the distal end, the opening at the distal end further comprising a sealed aperture, the drill being insertable into the proximal opening, the sealed aperture constructed and arranged to seal around the drill bit such that the drill is enclosed in the interior portion of the sterile barrier and only a portion of the drill bit extends exteriorly of the barrier;
providing a skull mounted locking trajectory guide;
mounting the trajectory guide on the patient's skull;
selecting a predetermined depth and adjusting the depth stop to the predetermined depth;
advancing the medical device to the skull and aligning it with the trajectory guide;
utilizing the medical device to cause the sterile drill bit to penetrate the skull the predetermined depth to which the depth stop is adjusted; and
removing the sterile drill bit from the skull.

24. The barrier of claim 20, wherein the aperture further includes an O-ring that is sized and shaped to seal around the drill bit.

25. A sterile barrier having an interior portion, a proximal end, a distal end, a proximal opening at the proximal end and an opening at the distal end, the opening at the distal end further comprising a sealed aperture, the sterile barrier constructed and arranged to enclose a medical device that includes a drill, such that the drill is enclosed in the interior portion of the sterile barrier and only a portion of a drill bit extends exteriorly of the barrier, and wherein the aperture includes an O-ring that is sized and shaped to seal around the drill bit.

* * * * *

UNITED STATES PATENT AND TRADEMARK OFFICE
CERTIFICATE OF CORRECTION

PATENT NO. : 6,716,215 B1
DATED : April 6, 2004
INVENTOR(S) : David et al.

It is certified that error appears in the above-identified patent and that said Letters Patent is hereby corrected as shown below:

Title page,
Item [56], References Cited, U.S. PATENT DOCUMENTS, after "Tankala et al." insert -- 408/1R --.

Column 7,
Line 65, after "spin" insert -- . --.

Signed and Sealed this

Twenty-fourth Day of August, 2004

JON W. DUDAS
*Director of the United States Patent and Trademark Office*